(12) United States Patent
Huth (10) Patent No.: US 6,982,079 B2
(45) Date of Patent: Jan. 3, 2006

(54) COMPOSITIONS FOR TREATING HYPEREMIA

(75) Inventor: Stanley W. Huth, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 446 days.

(21) Appl. No.: 10/133,094

(22) Filed: Apr. 26, 2002

(65) Prior Publication Data

US 2003/0203034 A1 Oct. 30, 2003

(51) Int. Cl.
*A61K 31/74* (2006.01)
*A61K 47/30* (2006.01)

(52) U.S. Cl. .............................. 424/78.04; 514/772.3; 514/781; 514/784; 514/785

(58) Field of Classification Search .............. 424/78.04, 424/427, 400, 401, 466, 422; 514/772.3, 514/781, 784, 785, 772.4, 772.6, 249
See application file for complete search history.

(56) References Cited

U.S. PATENT DOCUMENTS

| | | | |
|---|---|---|---|
| 3,278,447 A | 10/1966 | McNicholas | |
| 4,421,748 A | 12/1983 | Trager et al. | |
| 4,670,185 A | 6/1987 | Fujiwara et al. | |
| 5,188,826 A * | 2/1993 | Chandrasekaran et al. ........................ | 424/78.04 |
| 5,474,979 A | 12/1995 | Ding et al. | |
| 5,607,698 A | 3/1997 | Martin et al. | |
| 5,648,074 A | 7/1997 | Park et al. | |
| 5,725,887 A | 3/1998 | Martin et al. | |
| 5,858,346 A | 1/1999 | Vehige et al. | |
| 6,042,849 A | 3/2000 | Richardson et al. | |
| 6,071,539 A | 6/2000 | Robinson et al. | |
| 6,641,834 B2 * | 11/2003 | Olejnik et al. .............. | 424/427 |

FOREIGN PATENT DOCUMENTS

| | | |
|---|---|---|
| WO | WO0205822 | 1/2002 |
| WO | WO0228363 | 4/2002 |

OTHER PUBLICATIONS

Abstract Submitted to ARVO for Conference held Nov. 30, 2001: The Effect of Different CMC Materials in Artificial Tears in the Tear Layer on Contrast Sensitivity.
AQUALON® CMC, Physical and Chemical Properties, Hercules Incorporated, 1999.

* cited by examiner

*Primary Examiner*—Carlos A. Azpuru
(74) *Attorney, Agent, or Firm*—Stout, Uxa, Buyan & Mullins, LLP; Frank J. Uxa

(57) ABSTRACT

The present compositions advantageously treat hyperemia with substantially no added irritation to the eye. In one embodiment, the compositions include an ophthalmically acceptable carrier component, a vasoconstrictor component in an amount effective to treat hyperemia when the composition is administered to an eye, and a polyanionic component in an amount effective to provide lubrication to an eye when the compositions are administered to the eye.

17 Claims, 2 Drawing Sheets

COMPOSITIONS FOR TREATING HYPEREMIA

BACKGROUND OF THE INVENTION

The present invention relates to compositions including vasoconstrictor components for treating ocular hyperemia, preferably without resulting in significant eye irritation, and to methods for making and using such compositions. In one embodiment, the present invention relates to compositions effective to provide dual treatments for eye conditions, for example a dual treatment of hyperemia and dry eye.

Reddening or inflammation of the superficial tissues of the eye is a relatively common affliction since it usually accompanies various allergic reactions, such as hay fever allergies and the like, foreign body irritation in the eye, or eye fatigue. Such superficial conjunctival redness, often referred to as hyperemia or ocular hyperemia, can be the result of ciliary flush, dilation of the deep straight vessels of the episclera, and/or dilation of the superficial vessels of the conjunctiva.

Various types of palliative treatments have been used to treat this condition. The most common treatment includes the administration of eye drops which contain emollients and other ingredients designed to ease the discomfort due to the inflammation and to eliminate the redness associated with the condition. These treatments have not been entirely satisfactory, however.

For example, many commercially available eye drops include preservatives, an ingredient which may be quite harmful to the eye. Furthermore, many of the commercially available eye drops include ethylenediaminetetraacetic acid and/or salts thereof (EDTA), which may produce substantial discomfort when the eye drops are administered to the eye.

Also, these commercially available products often have pHs which are relatively acidic and can result in ocular irritation and/or discomfort.

Thus, there is a continued need to have improved compositions and methods for treating hyperemia.

SUMMARY OF THE INVENTION

New ophthalmic compositions useful for the treatment of hyperemia, and methods of making and using such compositions, have been discovered. The present compositions advantageously treat hyperemia with substantially no added irritation to the eye. These compositions are relatively straightforward, can be easily and cost effectively manufactured and can be used much like conventional eye drops. In one embodiment, the present compositions are effective to provide dual treatments for eye conditions, for example a dual treatment of hyperemia and dry eye.

In accordance with one broad aspect of the present invention, compositions are provided comprising an ophthalmically acceptable carrier component, preferably an aqueous carrier component, a vasoconstrictor component in an amount effective to treat hyperemia when the composition is administered to an eye, and a demulcent component, preferably a polyanionic component, in an amount effective to provide lubrication to an eye when the composition is administered to the eye. Advantageously, the present compositions are solutions, more preferably, liquid solutions, to facilitate convenient, consistent and effective use of the compositions.

In another broad aspect of the invention, the present compositions comprise an ophthalmically acceptable carrier component, a chlorine dioxide precursor component in an amount effective in preserving the composition, and a vasoconstrictor component in an amount effective to treat hyperemia when the composition is administered to an eye.

In a further broad aspect of the invention, compositions are provided comprising an ophthalmically acceptable, aqueous carrier component including at least one of a potassium component and an alkaline earth metal component, and a vasoconstrictor component in an amount effective to treat hyperemia when the composition is administered to an eye.

In an additional broad aspect of the invention, compositions are provided comprising an ophthalmically acceptable aqueous carrier component and a vasoconstrictor component in an amount effective to treat hyperemia when the composition is administered to an eye, the component having a pH in a range of about 6.7 to about 7.2 or about 7.4 or about 8.0.

Any suitable vasoconstrictor component may be employed in the present invention provided it is effective to treat ocular hyperemia. Advantageously, the vasoconstrictor is compatible with the other components of the composition, for example, is stable in the presence of the other components of the composition, for example for at least about 6 months or at least about 12 months, during storage. In one embodiment, the compositions are stable for about 36 months.

In a very useful embodiment, the vasoconstrictor component comprises at least one alpha-1-adrenergic agonist. For example, the vasoconstrictor component may be selected from the group consisting of tetrahydrozoline, ephedrine, naphazoline, phenylephrine, salts thereof and mixtures thereof. More preferably, the vasoconstrictor component is selected from tetrahydrozoline, salts thereof and mixtures thereof. In one useful embodiment, the present composition comprises about 0.001% or about 0.005% to about 0.15% or about 0.5% (w/v), more preferably about 0.01% to about 0.05% (w/v), of the vasoconstrictor component.

Any suitable demulcent may be employed in accordance with the invention, as long as it is compatible with other components in the composition. In one embodiment, the demulcent provides for lubrication to the eye. Non-limiting examples of demulcents include polyanionic components, hydroxyethylcellulose, hydroxypropylmethylcellulose, methylcellulose, dextran, gelatin, glycerin, polyethylene glycols, for example, polyethylene glycol 300, polyethylene glycol 400 and the like, polysorbate, propylene glycol, polyvinyl alcohol, polyvinyl pyrrolidone and the like and mixtures thereof. In one embodiment, the polyanionic component is selected from the group consisting of anionic cellulosic derivatives and mixtures thereof. In one embodiment, the polyanionic component is selected from the group consisting of carboxy methyl celluloses and mixtures thereof. Preferably, the present compositions comprise about 0.05% or about 0.1% to about 5% (w/v), more preferably about 0.15% or about 0.3% to about 2%, of a polyanionic component.

Still further in accordance with the present invention, the compositions comprise a carrier component. In one embodiment, the carrier component comprises water and has a pH in a range of about 6.7 to about 8.0, more preferably about 6.8 to about 7.2. In one embodiment, the carrier component comprises an electrolyte component. In one embodiment, the carrier component includes an alkaline earth metal component, for example, calcium components, magnesium components and mixtures thereof. In one embodiment, the alkaline earth metal component is present in an amount in a range of about 0.001% to about 0.05% (w/v), preferably about 0.005% to about 0.2% (w/v). In one embodiment, the carrier component comprises an electrolyte component. In one embodiment, the present compositions are free of an ethylenediaminetetraacetic acid (EDTA) component, for example, EDTA, salts of EDTA, and the like and mixtures thereof.

In one embodiment, the chlorine dioxide precursor component is present in an amount in a range of about 10 ppm to about 200 ppm. Preferably, the chlorine dioxide precursor component is the sole material effective as a preservative in the composition. In one embodiment, the chlorine dioxide precursor component includes at least one chlorite component. In one embodiment, the chlorine dioxide precursor component includes stabilized chlorine dioxide.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

The present invention involves ophthalmic compositions, which are advantageously ophthalmically acceptable, comprising an ophthalmically acceptable carrier component, a vasoconstrictor component and, optionally, a demulcent component, for example a polyanionic component.

A composition, carrier component or other material is "ophthalmically acceptable" when it is compatible with ocular tissue, that is, it does not cause significant or undue detrimental effects when brought into contact with ocular tissue. Preferably, the ophthalmically acceptable material is also compatible with other components of the present compositions.

The present compositions treat hyperemia advantageously with substantially no added irritation to the eye. In one embodiment, the present compositions treat hyperemia and dry eye syndrome advantageously with substantially no added irritation to the eye.

The present compositions preferably are solutions, although other forms, such as ointments, gels, and the like, may be employed.

Preferably, the present compositions meet, and pass, the EP-B antimicrobial preservative effectiveness criteria.

The present compositions include a vasoconstrictor component. In one embodiment, the vasoconstrictor component comprises an agent, for example a compound, which is effective in constricting a blood vessel of an eye, preferably a blood vessel on or near the ocular surface of the eye. In one embodiment, the vasoconstrictor component comprises an alpha-1-adrenergic agonist. Non-limiting examples of alpha-1-adrenergic agonists include tetrahydrozoline, ephedrine, naphazoline, phenylephrine, salts thereof and mixtures thereof. Preferably, the vasoconstrictor component is stable in the composition. For example, it is preferred that the vasoconstrictor component is not degraded, is soluble in the compositions and/or is therapeutically effective when the compositions are administered to the eye. Also, it is preferable that the vasoconstrictor component is stable in the compositions for more than about 10 months, preferably about 18 months, more preferably about 36 months or more, at storage conditions. In a preferred embodiment, the vasoconstrictor component comprises a tetrahydrozoline and/or a salt thereof.

The compositions comprise an amount of vasoconstrictor component effective to treat hyperemia when the compositions are administered to the eye. In one embodiment, the compositions comprise about 0.005% to about 0.15% (w/v) of the vasoconstrictor component. In one embodiment, the compositions comprise about 0.01% to about 0.10%, preferably 0.01% to about 0.05% of the vasoconstrictor component.

In one embodiment, the present compositions comprise a demulcent component. Without wishing to limit the invention to any theory or mechanism of operation, it is believed that the demulcent component is believed to be effective in lubricating an eye, for example, an eye which has, or has a propensity for having, dry eye syndrome. Non-limiting examples of demulcent components include polyanionic components, hydroxyethylcellulose, hydroxypropylmethylcellulose, methylcellulose, dextran, gelatin, glycerin, polyethylene glycols, for example, polyethylene glycol 300, polyethylene glycol 400 and the like, polysorbates, propylene glycol, polyvinyl alcohol, polyvinyl pyrrolidone and the like and mixtures thereof. See U.S. Pat. Nos. 4,421,748 and 5,474,979, the disclosure of each of which is incorporated in its entirety herein by reference. The demulcent component preferably is present, if at all, in a range of about 0.1% to about 5 (w/v).

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof.

Any suitable polyanionic component may be employed in accordance with the present invention provided that it functions as described herein and has no substantial detrimental effect on the compositions as a whole or on the eye to which the compositions are administered. The polyanionic component is preferably ophthalmically acceptable at the concentrations used. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the present compositions at ambient (room) temperature.

Examples of suitable polyanionic components useful in the present compositions include, without limitation, anionic cellulose derivatives, anionic acrylic acid-containing polymers, anionic methacrylic acid-containing polymers, anionic amino acid-containing polymers and mixtures thereof. Anionic cellulose derivatives are very useful in the present invention.

A particularly useful class of polyanionic components is one or more polymeric materials having multiple anionic charges. Examples include, but are not limited to:

metal carboxy methylcelluloses
    metal carboxy methylhydroxyethylcelluloses
    metal carboxy methylstarchs
    metal carboxy methylhydroxyethylstarchs
    hydrolyzed polyacrylamides and polyacrylonitriles
    heparin
    glucoaminoglycans
    hyaluronic acid
    chondroitin sulfate
    dermatan sulfate
    peptides and polypeptides
    alginic acid
    metal alginates
    homopolymers and copolymers of one or more of:
        acrylic and methacrylic acids
        metal acrylates and methacrylates
        vinylsulfonic acid
        metal vinylsulfonate
            amino acids, such as aspartic acid,
            glutamic acid and the like
        metal salts of amino acids
        p-styrenesulfonic acid
        metal p-styrenesulfonate
        2-methacryloyloxyethylsulfonic acids
        metal 2-methacryloyloxyethylsulfonates
        3-methacryloyloxy-2-hydroxypropylsulfonic acids
        metal 3-methacryloyloxy-2-hydroxypropylsulfonates
        2-acrylamido-2-methylpropanesulfonic acids
        metal 2-acrylamido-2-methylpropanesulfonates
        allylsulfonic acid
        metal allylsulfonate and the like.

Excellent results are achieved using polyanionic components selected from carboxy methylcelluloses and mixtures thereof, for example, alkali metal and/or alkaline earth metal carboxy methylcelluloses.

In one embodiment, carboxymethylcellulose is a cellulose ether, produced by reacting alkali cellulose with sodium monochloroacetate. Cellulose is a polymer composed of repeating cellobiose units. These, in turn, are composed of two anhydroglucose units (beta-glucopyranose residues). The number of anhydroglucose units, which are joined through 1,4 glucosidic linkages, represent the degree of polymerization. Each anhydroglucose unit contains three hydroxyl groups. By substituting carboxymethyl groups for some of these hydroxyls, sodium carboxymethylcellulose is obtained. The degree of substitution in the carboxymethylcellulose raw material used in this product formula may be 0.7, or an average of 7 carboxymethyl groups per 10 anhydroglucose units. A derivative of a carboxymethylcellulose may include a sucrose unit in the polymer.

In one embodiment, the compositions comprise about 0.05% to about 5.0% of the demulcent component, preferably polyanionic component. For example, compositions of the present invention may comprise about 0.05% to about 5%, preferably about 0.1% to about 3%, more preferably about 0.2% to about 2.5%, of a carboxymethylcellulose.

Preservatives which are commonly used in pharmaceutical compositions are often less effective when used in the presence of polyanionic components, for example carboxy methyl celluloses. In certain instances, this reduced preservative efficacy can be compensated for by using increased amounts of the preservative. However, where sensitive or delicate body tissue is involved, this approach may not be available since the preservative itself may cause some adverse reaction or sensitivity in the human or animal, to whom the compositions are administered.

In one embodiment, chlorine dioxide precursor components are effective as preservatives in the present compositions. Furthermore, chlorine dioxide precursor components have reduced toxicity and preferably substantially no toxicity to the eye when it is administered along with the present compositions.

Preferably, the present preservative components or components effective in aiding to preserve the compositions are effective in concentrations of less than about 500 ppm, for example, in the range of about 10 ppm or less to about 200 ppm. Preservative components or components effective in aiding to preserve the compositions in accordance with the present invention preferably include, but are not limited to, those which form complexes with the polyanionic component to a lesser extent than does benzalkonium chloride.

Examples of the components effective in aiding to preserve the compositions include, but are not limited to, oxidative preservative components, for example chlorine dioxide precursor components, peroxides, persalts, peracids, and the like, and mixtures thereof. Specific examples of chlorine dioxide precursor components useful as preservatives in accordance with the present invention include hypochlorite components, for example hypochlorites; chlorate components, for example chlorates; perchlorate components, for example perchlorates; and chlorite components. Examples of chlorite components include stabilized chlorine dioxide (SCD), metal chlorites, such as alkali metal and alkaline earth metal chlorites, and the like and mixtures therefor. Technical grade (or USP grade) sodium chlorite is a very useful preservative component. The exact chemical compositions of many chlorite components, for example, SCD, is not completely understood. The manufacture or production of certain chlorite components is described in McNicholas U.S. Pat. No. 3,278,447, the disclosure of which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purite® by Allergan, Inc. Other examples of oxidative preservative components include peroxy components. For example, trace amounts of peroxy components stabilized with a hydrogen peroxide stabilizer, such as diethylene triamine penta (methylene phosphonic acid) or 1-hydroxyethylidene-1,1-diphosphonic acid, may be utilized as a preservative for use in components designed to be used in the ocular environment. Also, virtually any peroxy component may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, may not be stabilized utilizing the present system. See, for example, Martin et al U.S. Pat. No. 5,725,887, the disclosure of which is incorporated in its entirety herein by reference.

In one embodiment of the invention, additional preservatives other than oxidative preservative components may be included in the compositions. These preservatives include quaternary ammonium compounds, in particular the mixture of alkyl benzyl dimethyl ammonium compounds and the like known generically as "benzalkonium chloride." Other preservatives which may be used include alkyl esters of p-hydroxybenzoic acid and the like and mixtures thereof, such as the mixture of methyl, ethyl, propyl and butyl esters which is sold under the trade name "Nipastat." In one embodiment, the present compositions are substantially free of benzalkonium chloride.

The carrier component is ophthalmically acceptable and may include one or more components which are effective in providing such ophthalmic acceptability and/or otherwise benefitting the composition and/or the eye to which the composition is administered and/or the patient whose eye is being treated. Advantageously, the carrier component is aqueous-based, for example, comprising a major amount that is at least about 50% by weight, of water. Other components which may be included in the carrier components include, without limitation, buffer components, tonicity components, preservative-components, pH adjustors, components commonly found in artificial tears, one or more alkali metal components, electrolyte component, alkaline metal earth components, and the like and mixtures thereof.

In one embodiment, the carrier component is free of a chelating agent. In one advantageous embodiment, the carrier component is free of EDTA components. The compositions of the present invention may be substantially free or completely free of EDTA.

The present compositions preferably include an effective amount of an electrolyte component, that is one or more electrolytes, for example, such as is found in natural tears and artificial tear formulations. Examples of particularly useful such electrolytes for inclusion in the present compositions include, without limitation, alkaline earth metal salts, such as alkaline earth metal inorganic salts, and mixtures thereof, e.g., calcium salts, magnesium salts and mixtures thereof. Very good results are obtained using an electrolyte component selected from calcium chloride, magnesium chloride and mixtures thereof.

The amount or concentration of such electrolyte component in the present compositions can vary widely and depends on various factors, for example, the specific electrolyte component being employed, the specific composition in which the electrolyte is to be included and the like factors. In one useful embodiment, the amount of the electrolyte component is chosen to at least partially resemble, or even substantially resemble, the electrolyte concentration in natural human tears. Preferably, the concentration of the electrolyte component is in the range of about 0.01% to about 0.5% or about 1% (w/v) of the present composition.

In a useful embodiment, the electrolyte component comprises an alkaline earth metal component and/or an alkali metal component. The compositions of the invention may advantageously comprise about 0.001% to about 0.05%, preferably 0.001% to about 0.02% (w/v), of an alkaline earth metal component. In one embodiment, the compositions comprise about 0.05% to about 0.5% (w/v) of an alkali metal component.

The alkaline metal earth component preferably comprises calcium components and/or magnesium components. The calcium component and the magnesium component comprise, for example, a calcium salt and a magnesium salt, respectively. Non-limiting examples of anionic counter ions for the calcium and magnesium salt include halide ions (such as chloride ions) and hydroxide ions. In one embodiment, the alkaline earth metal component comprises a calcium chloride and/or a magnesium chloride.

The alkali metal component preferably comprises sodium components and/or potassium components. The sodium component and the potassium component comprise, for example, a sodium salt and potassium salt, respectively. Non-limiting examples of anionic counter ions for the sodium and potassium salt include halide ions (such as chloride ions) and hydroxide ions. In one embodiment, the alkali metal component comprises a sodium chloride and/or a potassium chloride.

The present compositions preferably have viscosities in excess of the viscosity of water. In one embodiment, the viscosity of the present compositions is about 1 to about 10 cps (centipoise), more preferably in a range of about 2 to about 5 cps. In one embodiment, the viscosity of the compositions is about 10 cps to about 500 cps or about 1,000 cps. Advantageously, the viscosity of the present compositions is in a range of about 15 cps or about 30 cps or about 70 to about 150 cps or about 200 cps or about 300 cps or about 500 cps. The viscosity of the present compositions may be measured in any suitable, for example, conventional manner. A conventional Brookfield viscometer measuring such viscosities may be employed.

In one very useful embodiment the carrier component includes at least one of the following: an effective amount of a buffer component; an effective amount of a tonicity component; an effective amount of a preservative component; and water.

These additional components preferably are ophthalmically acceptable and can be chosen from materials which are conventionally employed in ophthalmic compositions, for example, compositions used to treat eyes afflicted with dry eye syndrome, artificial tear formulations and the like.

Acceptable effective concentrations for these additional components in the compositions of the invention are readily apparent to the skilled practitioner.

The carrier component preferably includes an effective amount of a tonicity adjusting component to provide the compositions with the desired tonicity. The carrier component preferably includes a buffer component which is present in an amount effective to maintain the pH of the compositions in the desired range.

In one embodiment, the pH of the compositions is about 6 to about 8, preferably about 6.7 to about 7.5, more preferably about 6.7 to about 7.2, even more preferably, about 6.9 or about 7.0 to about 7.2.

Among the suitable tonicity adjusting components that may be employed are those conventionally used in ophthalmic compositions, such as one or more various inorganic salts and the like. Sodium borate, boric acid, sodium chloride, potassium chloride, mannitol, dextrose, glycerin, propylene glycol and the like and mixtures thereof are very useful tonicity adjusting components. Among the suitable buffer components or buffering agents that may be employed are those conventionally used in ophthalmic compositions. The buffer salts include alkali metal, alkaline earth metal and/or ammonium salts. Conventional organic buffers, such as Goode's buffer and the like, may also be employed.

The present compositions may be prepared using conventional procedures and techniques. For example, the present compositions can be prepared by blending the components together, such as in one bulk.

In one particularly useful embodiment, a solution of the polyanionic component and purified water is obtained. Separately, the other components to be included in the final composition are solubilized in purified water. The two solutions are combined into a single solution. This latter solution is sterile filtered, for example, through a 0.2 micron sterilizing pre-filter, such as that sold by Millipore under the tradename Milliguard. The final solution is sterile filtered once again, to provide a clear, smooth solution which is then aseptically filled into containers.

In one embodiment, compositions are featured comprising an ophthalmically acceptable carrier component, a vasoconstrictor component in an amount effective to treat hyperemia when the composition is administered to an eye, and a polyanionic component in an amount effective to provide lubrication to an eye when the compositions are administered to the eye. Preferably, the compositions are in a solution form, for example not gel form. In one embodiment, the present compositions are free of a chelating agent, for example EGTA and/or EDTA. In a preferred embodiment, the present compositions are effective to treat hyperemia in subjects, for example human subjects, effectively without inducing substantial irritation. Also in a preferred embodiment, the present compositions are able to treat hyperemia and dry eye conditions in subjects, for example human subjects, effectively without inducing substantial irritation.

In one embodiment, compositions are featured comprising an ophthalmically acceptable carrier component, a chlorine dioxide precursor component in an amount effective in preserving the composition, a vasoconstrictor component in an amount effective to treat hyperemia when the composition is administered to an eye and a demulcent component, selected from the group consisting of a polyanionic component, hydroxyethylcellulose, hydroxypropylmethylcellulose, methylcellulose, dextran, gelatin, glycerin, polyethylene glycol 300, polyethylene glycol 400, polysorbate, propylene glycol, polyvinyl alcohol, N-vinyl pyrrolidone and mixtures thereof.

In one embodiment, compositions are featured comprising an ophthalmically acceptable, aqueous carrier component including an alkaline earth metal component, and a vasoconstrictor component in an amount effective to treat hyperemia when the composition is administered to an eye. Preferably, the composition has a pH in a range of about 6.8 to about 7.4, preferably 7.2. Also, preferably, the compositions are free of a chelating component, for example EGTA and/or EDTA.

The present compositions may be effectively used, as needed, by methods which comprise administering an effective amount of the compositions to an eye in need of treatment for hyperemia, and optionally dryness. The administering step may be repeated as needed to provide effective reduction of redness, and optionally lubrication, of such eye. The mode of administration of the present compositions depends on the form of the composition. For example, if the composition is a solution, drops of the composition may be applied to the eye, e.g., from a conventional eye dropper. In general, the present compositions may be applied to the surface of the eye in substantially the same way as conventional ophthalmic compositions are applied. Such administration of the present compositions does provide substantial and unexpected benefits, as described elsewhere herein.

The following non-limiting examples illustrate certain aspects of the present invention.

EXAMPLE 1

A composition is prepared by blending the various materials together and has a make-up as shown in Table 1.

TABLE 1

| Ingredients | % w/v |
| --- | --- |
| Tetrahydrozoline HCl, USP | 0.05 |
| Sodium Carboxymethylcellulose, USP[1] | 0.5 |
| Sodium Chloride, PhEur/USP | 0.39 |
| Boric Acid, NF/PhEur | 0.60 |
| Sodium Borate Decahydrate, NF | 0.035 |
| Potassium Chloride, USP | 0.14 |
| Calcium Chloride Dihydrate, USP | 0.006 |
| Magnesium Chloride Hexahydrate, USP | 0.006 |
| Purite ®[2] | 0.0055 |
| Sodium Hydroxide 1 N, NF | Adjust pH to 7.2 |
| Hydrochloric Acid 1 N, NF | Adjust pH to 7.2 |
| Purified Water, UPS | q.s. ad |

[1]Low Viscosity.
[2]Purite ® is a registered trademark of Allergan, Inc. for stabilized chlorine dioxide.

The stability of this composition is evaluated at several different temperatures and humidity conditions, according to standard procedures. This tetrahydrozoline hydrochloride-containing composition is found to be sufficiently stable to have at least an 18-month shelf life. Thus, this composition would be entitled to be labeled with at least an 18 month expiration date.

EXAMPLE 2

A second composition is prepared and tested for stability substantially as set forth in Example 1. The second composition has an identical make-up to the composition of Example 1 with the exception that the Purite® concentration in the second composition is 0.0050% (w/v).

The stability testing of this second composition demonstrates that this composition has stability similar to that of the composition of Example 1.

EXAMPLE 3 (Comparative)

Another composition is prepared and tested for stability substantially are set forth in Example 1. This other composition has an identical make-up to the Example 1 composition with the exception that the other compositions included 0.012% (w/v) of naphazoline hydrochloride (in place of the tetrahydrozoline hydrochloride).

The stability testing surprisingly found that the composition of Example 3, containing naphazoline hydrochloride, has substantially reduced stability relative to the Example 1 composition. This stability difference is unexpected in view of the similarities in chemical structure between tetrahydrozoline hydrochloride and naphazoline hydrochloride.

EXAMPLE 4

Vasoconstrictor Efficacy Comparison in New Zealand Albino Rabbits.

The composition of Example 2, Visine® Original composition and Visine® L.R. composition are tested in an animal model for their abilities to treat red eye (hyperemia) and irritability effects.

Visine® Original composition includes the following: tetrahydrozoline hydrochloride 0.05% (w/v), benzalkonium chloride 0.01% (w/v), boric acid, edetate disodium 0.1% (w/v), sodium borate, sodium chloride and purified water. The pH is determined to be 6.38. The osmolality is measured and found to be 289 mOsm/kg.

Visine® L.R. composition includes the following: oxymetazoline hydrochloride 0.03% (w/v), benzalkonium chloride 0.01% (w/v), boric acid, edetate disodium 0.1%, sodium borate, sodium chloride and purified water. The pH is determined to be 6.34. The osmolality is measured and found to be 286 mOsm/kg.

Red eye, or ocular hyperemia, is scored on a 4 grade scale: 0 (no redness); +1 (some redness); +2 (moderate redness); and +3 (majority of conjunctiva red).

One drop per eye per animal of arachidonic acid 0.015% (w/v), with 0.45% (w/v) alpha-cyclodextrin, pH 7.7 is used to induce sufficient initial red eye (+2) without discomfort in 10 minutes or less.

Two animals, one eye each, are used per vasoconstrictor solution. A single dose of 2 drops of vasoconstrictor solution per eye is used.

All 3 solutions exhibited equal efficacy in eliminating red eye (+2 to +1 hyperemia in 5–10 minutes, no redness at 2 hours post dosing). No irritation is noted with the Example 2 composition or Visine® Original composition. Significant irritation is noted with Visine® L.R composition.

EXAMPLE 5

Vasoconstrictor Efficacy Comparison in New Zealand Albino Rabbits.

The composition of Example 1, Visine® Original composition, Visine® L.R. composition, All Clear® composition and All Clear® AR composition are tested in an animal model for their abilities to treat red eye and irritability effects.

All Clear® composition includes the following: maphazoline hydrochloride 0.012% (w/v), benzalkonium chloride 0.01% (w/v) and polyethylene glycol 3000.2% (w/v). The pH is determined to be 6.02.

All Clear® AR composition includes the following: naphazoline hydrochloride 0.03% (w/v), benzalkonium chloride 0.01% (w/v) and hydroxypropylmethylcellulose (HPMC) 0.5% (w/v). The pH is determined to be 5.97.

Three (3) rabbits are used to test each solution. All animals have an initial hyperemia score of +2. Two drops of test solution are applied to one eye of each test animal. Ocular hyperemia is graded at 2, 5, 10, 20, 30, 40, 50, 60, 90, 120 and 180 minutes. The identity of test sample is masked from the graders. Hyperemia scores are averaged for each test solution.

All test samples are effective in reducing or eliminating hyperemia in 5 to 10 minutes. Visine® Original composition and All Clear® composition exhibit substantial "rebound" red eye after the initial decrease in red eye. All Clear® AR composition and the Example 1 composition exhibit some modest rebound red eye with reduced rebound relative to Visine® Original composition and All Clear® composition. Visine® L.R. composition does not exhibit any rebound red eye. The All Clear® composition and All Clear® AR composition exhibit the fastest elimination of all redness, followed by the Example I composition, then the Visine® composition and lastly, the Visine® L.R. composition. No discomfort is noted with any of the test solutions.

EXAMPLE 6

Ocular Comfort Comparison in Human Subjects

The Example 1 composition and the Visine® Original composition are tested on seven human subjects for ocular comfort. One to two drops of a selected composition are self administered to one eye by all subjects. Four subjects (1, 2, 3, 4) experience no burning, stinging or superior temporal aching with the Example I composition.

Five subjects (1, 4, 5, 6, 7) test the Visine® Original composition. Of these five, three subjects (1, 4, and 7) experience substantial burning and stinging in the first 1–2 minutes, lasting about 10 seconds, and two subjects (1 and 7) experience aching in the superior temporal region of the eye for a number of minutes following the initial burning and stinging.

Overall, the present compositions, as exemplified by the Example 1 composition and the Example 2 composition, have highly acceptable stability, or shelf life, and efficacy in treating red eye, or hyperemia. For example, the present compositions are found to provide as good as or better hyperemia treating efficacy relative to all the commercially available, vasoconstrictor-containing products tested. In addition, and importantly, the present compositions provide such acceptable hyperemia treatment efficacy results with little or no eye irritation. Without wishing to limit the present invention to any particular theory or mechanism of operation, it is believed that the outstanding combination of beneficial properties provided by the present compositions is at least in part due to one or more of the following: the presence of both a vasoconstrictor component and a demulcent component, preferably a polyanionic component; the presence of chlorine dioxide precursor as a preservative; a more ophthalmically acceptable pH, for example, in a range of about 6.7 to about 7.2 or about 7.4 or about 8; the presence of at least one of a potassium component and an alkaline earth metal component; and/or the absence of an EDTA component. In any event, the present compositions are relatively straightforward, can be made using conventional and well known techniques and procedures and provide one or more highly desirable benefits.

EXAMPLE 7

Ocular Comfort Comparison in Human Subjects

Approximately 170 consumers, who are current daily users of artificial tear products, are enrolled into a paired-comparison study, evaluating the comfort and acceptability of the composition of Example 1 to that of Visine® Original. Respondents' eyes are randomized to receive one drop of either the composition of Example 1 or Visine® Original, with the other eye receiving the other product. Respondents and evaluators are masked as to the identity of the products. Respondents rate comfort and acceptability measures on a scale of 0–100. Respondents answer preference questions as preferring one product or the other, or not expressing a preference.

Approximately 38% of the respondents state that they are current users of Visine® Original eyedrops.

166 consumers complete the evaluation. The composition of Example 1 is perceived as being more "soothing" (99% level of significance, P=0.01) and more "refreshing" (91% level of significance, P=0.09) upon instillation than Visine® Original. The composition of Example 1 also exhibits less eye ache (88% level of significance, P=0.12).

Acceptability variables are reassessed 15 minutes after instillation of medication. At this time point, the composition of Example 1 is still perceived more "refreshing" (93% level of significance, P=0.07) than Visine® Original. Additionally Visine® Original is perceived as causing more "burning/stinging" (95% level of significance, P=0.05) and more "eye ache" (92% level of significance, P=0.08) than the composition of Example 1.

Overall preference ratings are assessed at the end of the 15-minute period. The composition of Example 1 is preferred over Visine® Original on an overall basis (91% level of significance, P=0.09) and for the treatment of dry eye (93% level of significance, P=0.07). Although it is not statistically significant, there is a strong directional preference for the composition of Example 1 over Visine® Original for the treatment of red eye.

EXAMPLE 8

Comparison of Relief of Red Eye in Human Subjects

The composition of Example 1 is utilized in a double-masked prospective clinical trial. Visine® Original was repackaged into the same bottles as the composition of Example 1 and the vehicle. The results are unmasked only after all subjects are completed.

A total of 91 participants are enrolled in the study, 31 in the composition of Example 1 group, 30 in the control group (vehicle) and 30 in the comparison (Visine®) group (randomly assigned). The vehicle is the composition of Example 1 without the tetrahydrozoline hydrochloride. The acute phase is during the first 6 hours after the first instillation of the drops. A single drop is instilled in each eye, that is into the lower conjuctival sac. Measurements of red eye are taken once every minute for the first 5 minutes, then every 20 minutes for the first hour, and once at the 2, 4 and 6 hour points. On the subsequent days during the chronic phase, participants applied 1 drop, in each eye, four times a day. On the $3^{rd}$ and $7^{th}$ days, measurements are made within approximately 2 hours of the most recent drop instillation and single subjective and objective measurements of red eye are taken. On the $8^{th}$ day, after discontinuation of the drops, single subjective and objective measurements of red eye are repeated to determine if there are any rebound effects.

A Spectrascan650® Photometer by Photoresearch® is used to make objective measurements of redness of the conjunctiva of the eye under fixed illumination conditions. The instrument measures chromaticity in CIE u' units. The instrument is mounted on a base with a chin and forehead rest.

The participant sits at the instrument and fixated on an LED on the nasal side of the photometer. The examiner positions the measuring spot, which covers a circular area of 5 mm on the bulbar conjunctiva, about 2 mm from the limbus. The examiner focuses the instrument by moving the instrument forwards and backwards. The adjustment of the focus of the objective lens always remains unchanged and the lateral position of the instrument as well as the illumination is kept constant. Measurements are taken on the temporal conjunctiva and data are recorded along with the exact time. Redness (in this instance CIE u') values are recorded for temporal conjunctivas of the both eyes after biomicroscopy examination and then, after the instillation of the drop.

Figure 1:
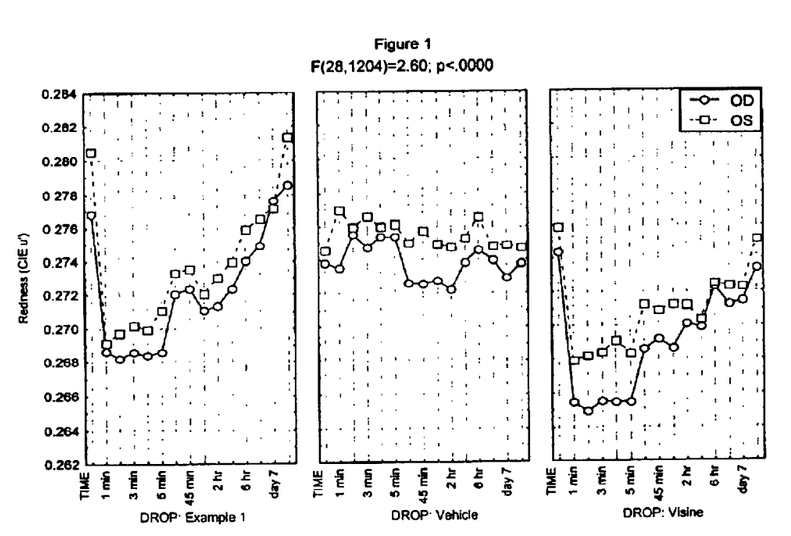
FIG. 1 shows a presentation of eye redness data from a comparative study of a composition, in accordance with the present invention and Visine® eye drops.

FIG. 1 shows redness data with the x axes being measurement time (note different step sizes) and the y-axes being redness (chromaticity) of the temporal bulbar conjunctiva (CIE u'). Each panel shows data for the right and left eye.

As shown, there is significant reduction in redness for both the composition of Example 1 and Visine®, while the control (vehicle) measurements are approximately constant across time.

Figure 2A:
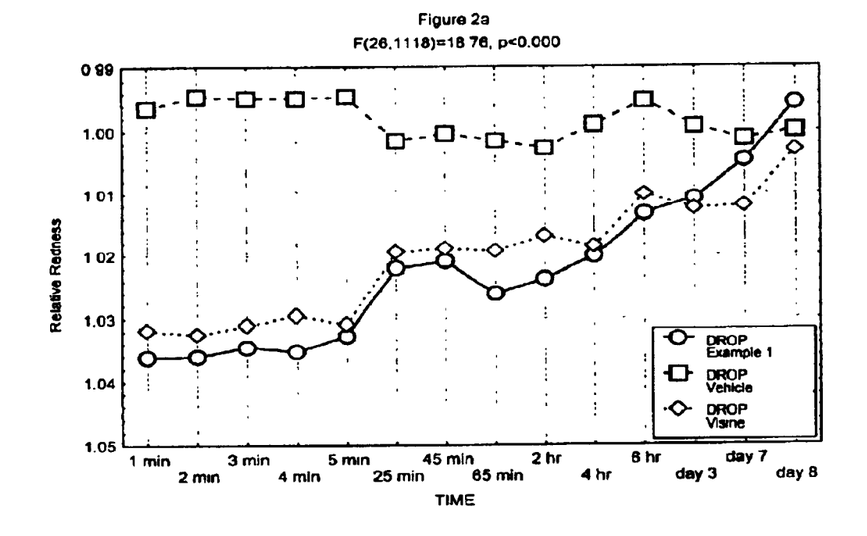
FIG. 2a shows another presentation of these redness data.
Figure 2B:
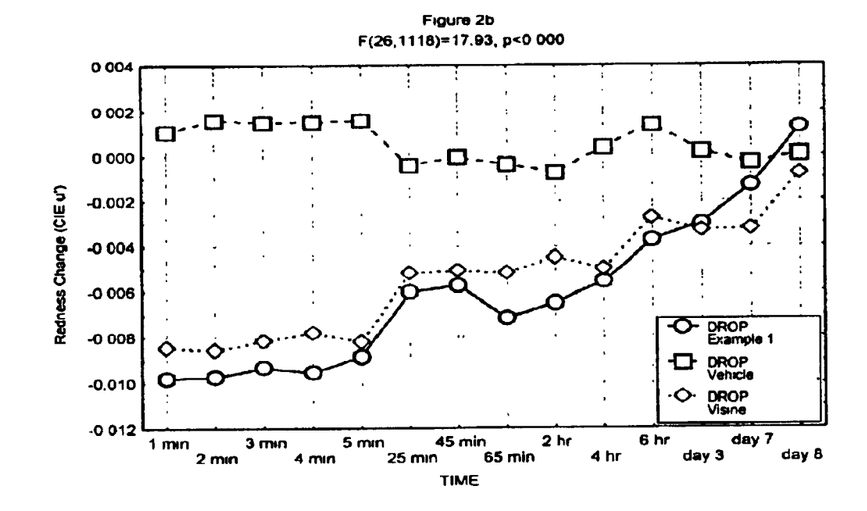
FIG. 2b shows a further presentation of these redness data.

To facilitate visual inspection and deal with a number of technical issues including outliers, change from baseline, averaged across eyes, is shown in FIGS. 2a and 2b. Change is expressed as both arithmetic difference from baseline (FIG. 2b) and the ratio to baseline (FIG. 2a). For both, on the y-axis, lower is less red.

Again, as there are significant differences between drops, with tests for simple effects and post hoc testing showing no differences between Visine® and the composition of Example 1 and both being different from control (vehicle) up to (and including) day 3, the third to last measurement. During acute, chronic and post-chronic phases, there is substantially no "rebound redness".

The results of this study provide very clear evidence of the following:

1) Redness reduction with Visine® and the composition of Example 1 is approximately the same when measured objectively. Equivalent results is obtained when redness is assessed subjectively by the examiner using traditional scales and when rated by the user of the drops; and 2) The effects of these drops in reducing redness compared to a non-pharmacologically active product is significant.

The disclosure of Vehige et al U.S. Pat. No. 5,858,346 is incorporated in its entirety herein by reference.

While this invention has been described with respect to various specific examples and embodiments, it is to be understood that the invention is not limited thereto and that it can be variously practiced with the scope of the following claims.

What is claimed is:

1. A composition comprising:
   an ophthalmically acceptable carrier component;
   a vasoconstrictor component in an amount effective to treat hyperemia when the composition is administered to an eye; and
   a polyanionic component in an amount effective to provide lubrication to an eye when the composition is administered to an eye, the composition being a solution.

2. The composition of claim 1 wherein the vasoconstrictor component comprises an alpha-1-adrenergic agonist.

3. The composition of claim 1 wherein the vasoconstrictor component is selected from the group consisting of tetrahydrozoline, ephedrine, naphazoline, phenylephrine, salts thereof and mixtures thereof.

4. The composition of claim 1 wherein the vasoconstrictor component is selected from the group consisting of tetrahydrozoline, salts thereof and mixtures thereof.

5. The composition of claim 1 comprising about 0.001% to about 0.05% (w/v) of the vasoconstrictor component.

6. The composition of claim 1 wherein the polyanionic component is selected from the group consisting of anionic cellulosic derivatives and mixtures thereof.

7. The composition of claim 1 wherein the polyanionic component is selected from the group consisting of carboxy methyl celluloses and mixtures thereof.

8. The composition of claim 1 wherein the polyanionic component is selected from the group consisting of anionic homopolymers and copolymers comprising units of one or more of acrylic acid, methacrylic acid, metal acrylates and metal methacrylates, and mixtures thereof.

9. The composition of claim 1 comprising about 0.1% to about 5% (w/v) of the polyanionic component.

10. The composition of claim 1 wherein the carrier component comprises water.

11. The composition of claim 10 which has a pH in a range of about 6.7 to about 8.0.

12. The composition of claim 1 wherein the carrier component includes at least one of a potassium component and an alkaline earth metal component.

13. The composition of claim 12 wherein the alkaline earth metal component is present and is selected from the group consisting of calcium components, magnesium components and mixtures thereof.

14. The composition of claim 12 wherein the alkaline earth metal component is present in an amount in a range of about 0.001% to about 0.05% (w/v).

15. The composition of claim 1 wherein the carrier component includes at least one of an effective amount of a buffer component and an effective amount of a tonicity adjuster component.

16. The composition of claim 1 which further comprises a chlorine dioxide precursor component in an amount effective in preserving the composition.

17. The composition of claim 1 which is free of an ethylenediaminetetraacetic acid component.

* * * * *